United States Patent [19]
Olstein

[11] Patent Number: 5,453,248
[45] Date of Patent: Sep. 26, 1995

[54] CROSS-LINKED GAS PERMEABLE MEMBRANE OF A CURED PERFLUORINATED URETHANE POLYMER, AND OPTICAL GAS SENSORS FABRICATED THEREWITH

[75] Inventor: Alan Olstein, Mendota Heights, Minn.

[73] Assignee: Optical Sensors Incorporated, Minneapolis, Minn.

[21] Appl. No.: 911,175

[22] Filed: Aug. 12, 1992

Related U.S. Application Data

[63] Continuation-in-part of Ser. No. 848,627, Mar. 9, 1992, abandoned.
[51] Int. Cl.$^6$ .................................................. G01N 21/64
[52] U.S. Cl. ........................... 422/82.07; 422/82.11; 422/82.08; 528/70; 427/165; 250/458.1
[58] Field of Search .................... 528/65, 70, 75; 522/96, 97; 422/82.06, 82.07, 82.08, 82.09, 82.11; 436/166, 169, 136, 138, 133; 427/165; 250/458.1

[56] References Cited

U.S. PATENT DOCUMENTS

| | | |
|---|---|---|
| 3,671,497 | 6/1972 | Low et al. . |
| 4,321,057 | 3/1982 | Buckles . |
| 4,508,916 | 4/1985 | Newell et al. . |
| 4,549,012 | 10/1985 | Sharma . |
| 4,785,814 | 11/1988 | Kane . |
| 4,816,130 | 3/1989 | Karakelle et al. . |
| 4,842,783 | 6/1989 | Blaylock . |
| 4,935,480 | 6/1990 | Zdrahala et al. . |
| 5,004,790 | 4/1991 | Harnish et al. . |
| 5,032,666 | 7/1991 | Hu et al. . |
| 5,151,535 | 9/1992 | Fuchikami et al. . |
| 5,266,271 | 11/1993 | Bankert et al. ............... 422/82.07 |
| 5,277,872 | 1/1994 | Bankert et al. ............... 422/82.07 |

FOREIGN PATENT DOCUMENTS

| | | |
|---|---|---|
| 322624 | of 0000 | European Pat. Off. . |
| 224201 | of 0000 | European Pat. Off. . |
| 2132348 | of 0000 | United Kingdom . |
| WO88/05533 | of 0000 | WIPO . |

OTHER PUBLICATIONS

H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53.

*Primary Examiner*—Jeffrey R. Snay
*Attorney, Agent, or Firm*—Reed & Robins

[57] ABSTRACT

An optical sensor is provided for measuring dissolved gases such as $O_2$ or $CO_2$ in a fluid sample. The sensor is formulated so as to contain a gas permeable membrane of a cured perfluorinated urethane polymer and, incorporated therein, a gas-sensitive indicator component. Methods for making and using the membrane and sensor are provided as well.

39 Claims, 1 Drawing Sheet

CROSS-LINKED GAS PERMEABLE MEMBRANE OF A CURED PERFLUORINATED URETHANE POLYMER, AND OPTICAL GAS SENSORS FABRICATED THEREWITH

CROSS-REFERENCE TO RELATED APPLICATION

This application is a continuation-in-part of U.S. patent application Ser. No. 07/848,627, filed Mar. 9, 1992, now abandoned.

TECHNICAL FIELD

The present invention relates generally to optical sensors for measuring dissolved gases in a fluid, and more particularly relates to a novel optical sensor system containing a gas permeable membrane of a cured perfluorinated urethane polymer.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," *Analytical Chemistry*, Vol. 56, No. 1, January 1984, each of which is incorporated by reference herein.

Publications such as these generally illustrate that is it known to incorporate a chemical sensor into a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to thereby provide especially sensitive remote monitoring capabilities. Chemical sensor compositions that are incorporated at the distal end of fiber optic sensors are often configured as membranes that are secured at the distal tip end of the waveguide device or optrode.

Gas sensors of this general type are useful in monitoring gas concentrations such as oxygen and carbon dioxide in bloodstreams and the like. Also, it is sometimes desirable to provide sensors that monitor other parameters such as pH. Ion concentrations can also be detected, such as potassium, sodium, calcium and metal ions.

A typical gas-sensor device positions the sensor material at a generally distal location with the assistance of various different support means. Support means must be such as to permit interaction between the gas indicator and the substance being subjected to monitoring, measurement and/or detection. Known approaches in this regard include the use of permeable membranes and composites incorporating micro-encapsulation. With certain arrangements, it is desirable to incorporate membrane components into these types of devices. These membrane components must possess certain properties in order to be particularly advantageous. Many membrane materials have some advantageous properties but also have shortcomings. Generally speaking, the materials must be biocompatible, they must be permeable to the gas being monitored, and they must be capable of supporting the gas-sensitive indicator, while at the same time possessing the strength adequate to permit maneuvering of the device without concern about damage to the gas sensor. It is also desirable to have these materials be photocurable in order to facilitate locating the gas sensor composite on the device.

In summary, the present invention is addressed to novel polymer compositions which have been found to be particularly suitable for use as membranes and membrane-like components which incorporate gas-sensitive indicators to form the active gas sensor component of a gas sensor device. The polymer compositions are particularly useful in fiber optic sensors for measuring dissolved gases, particularly $O_2$ or $CO_2$, in a fluid. The polymer compositions are cured perfluorinated urethane polymers formed by cross-linking a perfluorinated urethane precursor using a suitable cross-linking agent. Relative to previously known and used gas sensors, the present polymer compositions provide for gas sensors of superior sensitivity, resolution, solvent resistance and photostability. In addition, gas sensors fabricated with the present polymer compositions display increased resistance to fluid flow and shear, because of increased adhesion of the polymer composition to the fiber substrate. Also, the polymer compositions described herein generally require a lower level of cross-linking agent, and will typically contain very little or no residual monomer after cure. Finally, the present polymer compositions have been found to increase the life of the gas sensor by eight- to ten-fold.

OVERVIEW OF RELATED ART

The following references relate to one or more aspects of the present invention:

U.S. Pat. No. 3,671,497 to Low et al. describes a polyurethane resin derived from a hydroxy-terminated perfluoroether.

U.S. Pat. No. 4,549,012 to Sharma describes perfluoroacyl modified cellulose acetate polymers which are stated to be useful in forming thin gas-permeable membranes.

U.S. Pat. No. 4,785,814 to Kane describes an optical probe useful for measuring pH and oxygen and blood. The device includes a membrane constructed of a hydrophilic porous material containing a pH-sensitive dye.

U.S. Pat. No. 4,842,783 to Blaylock describes a fiber optic chemical sensor which, at the distal end of the optical fiber, is provided with a photocrosslinked polymeric gel having a dye adsorbed therein.

U.S. Pat. No. 4,935,480 to Zdrahala et al. relates to fluorinated polyether urethanes and medical devices (e.g., catheters) fabricated therefrom.

U.S. Pat. No. 5,032,666 shows a thermoplastic fluorinated polyurethaneurea having free amino groups, and discloses the use of such polymers in forming antithrombogenic surfaces in medical devices.

PCT Publication No. WO88/05533, inventors Klainer et al., describes a fiber optic sensing device for measuring a chemical or physiological parameter of a body fluid or tissue, in which a polymer containing photoactive moieties is directly bound to the fiber optic tip.

European Patent Publication No. 224,201, inventors Caporiccio et al., describes a process for conversion of high molecular weight perfluoropolyethers to provide lower molecular weight, neutral perfluoropolyethers.

European Patent Publication No. 322,624, inventors Birkle et al., describes perfluorinated polyethers useful in electrical applications.

U.K. Patent Application No. 2,132,348 to Bacon et al. describes an oxygen sensor in which the gas sensitive indicator component is a luminescent organometallic complex.

H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53, identify a number of materials which will act to catalyze radiation curing of multifunctional monomers or oligomers.

SUMMARY OF THE INVENTION

Accordingly, it is a primary object of the invention to address the above-mentioned needs in the art, by providing an optical sensor for measuring dissolved gases in a fluid, wherein the sensor has improved sensitivity, resolution, solvent resistance, photostability, and resistance to shear.

It is another object of the invention to address these needs by providing an optical gas sensor which includes a membrane of a cured perfluorinated urethane polymer and a gas-sensitive indicator component.

It is still another object of the invention to provide such a sensor in which the perfluorinated urethane polymer comprises a perfluorinated polyurethane acrylate.

It is yet another object of the invention to provide a gas permeable membrane for use in such a sensor, which comprises a polymeric matrix of a cured perfluorinated urethane polymer, and, incorporated therein, a gas-sensitive indicator component.

It is a further object of the invention to provide such a membrane in which the perfluorinated urethane polymer comprises a perfluorinated polyurethane acrylate.

It is still a further object of the invention to provide a method of making an optical gas sensor by polymerizing a precursor to a perfluorinated urethane polymer on a fiber optic tip.

It is yet a further object of the invention to provide a method of making an optical gas sensor by polymerizing a photocurable polymeric precursor on a fiber optic tip by irradiating the precursor through the fiber.

Additional objects, advantages and novel features of the invention will be set forth in part in the description which follows, and in part will become apparent to those skilled in the art upon examination of the following, or may be learned by practice of the invention.

In one aspect, a cross-linked gas permeable membrane useful in optical gas sensors is provided, wherein the membrane comprises a polymeric matrix of a cured perfluorinated urethane polymer, and, incorporated therein, a gas-sensitive indicator component as will be described in detail herein. In a preferred embodiment, the perfluorinated urethane polymer is a perfluorinated polyurethane acrylate which comprises a perfluorinated polyurethane acrylate precursor cross-linked with a cross-linking agent.

In another aspect, an optical sensor is provided for measuring dissolved gases such as $O_2$ or $CO_2$, which comprises an optical waveguide having a distal end portion for monitoring a gas component within a fluid, e.g., a bloodstream or the like, and a proximal end portion for communication with means for receiving a signal from the distal end portion, and wherein the distal end portion has a gas sensor means comprising a cross-linked gas permeable membrane as summarized above and as will be described in detail below.

In still another aspect, a method is provided for making the aforementioned optical sensor. In a preferred embodiment, the method involves polymerization of a photocurable polymeric precursor on the fiber optic tip, by irradiating the precursor-coated tip through the optical fiber. In another embodiment, polymerization of a perfluorinated urethane polymer precursor may be effected by contacting the precursor-coated tip with a cross-linking agent in solution or the like.

In yet another aspect, a cured perfluorinated urethane polymer is provided which is useful in the above-mentioned contexts.

BRIEF DESCRIPTION OF THE DRAWINGS

In the course of this description, reference will be made to the attached drawings, wherein.

DETAILED DESCRIPTION OF THE INVENTION

Figure 1:
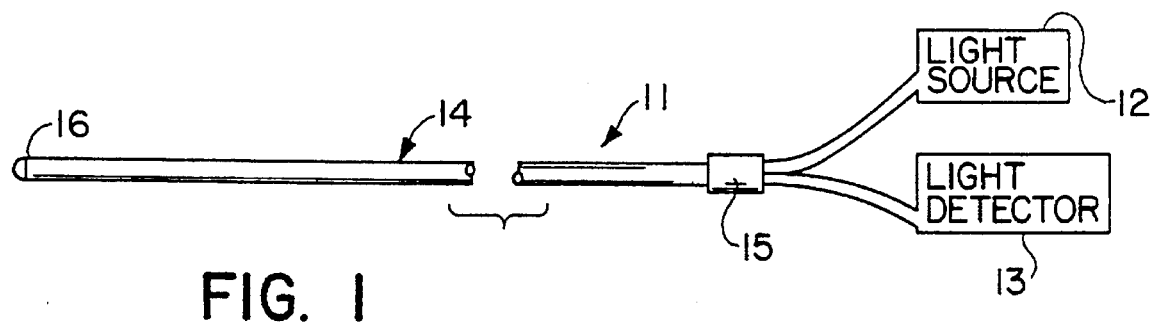
FIG. 1 is a generally schematic view of a chemical sensor device according to the present invention which is incorporated in a fiber optic gas sensor device.
Figure 2:
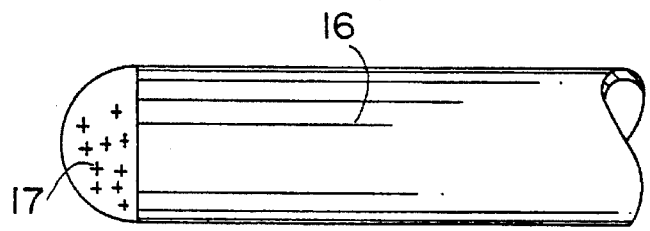
FIG. 2 is an enlarged, detail and generally schematic view of the distal end portion of a gas sensor device generally in accordance with FIG. 1 and incorporating a monolithic cross-linked fluorocarbon polymer according to the present invention.

Before the present compositions, membranes, sensors and methods of manufacture are disclosed and described, it is to be understood that this invention is not limited to specific sensor formats, specific membrane compositions, or particular cross-linking agents or curing processes, as such may, of course, vary. It is also to be understood that the terminology used herein is for the purpose of describing particular embodiments only and is not intended to be limiting.

It must be noted that, as used in the specification and the appended claims, the singular forms "a" "an" and "the" include plural referents unless the context clearly dictates otherwise. Thus, for example, reference to "a perfluorinated urethane polymer" includes mixtures of such polymers, reference to "a perfluorinated urethane polymer precursor" includes mixtures of two or more such polymers, reference to "a cross-linking agent" includes reference to two or more cross-linking agents, and the like.

In describing and claiming the present invention, the following terminology will be used in accordance with the definitions set out below.

The term "polymer" as used herein is intended to include both oligomeric and polymeric materials, i.e., compounds which include two or more monomeric units. Similarly, the term "perfluorinated polyether" linkage is intended to mean a linkage containing at least two perfluorinated ether mer units, i.e., ether mer units in which each hydrogen atom normally present has been replaced by a fluorine atom.

The term "urethane" is used herein in its conventional sense to denote organic compounds containing a recurring —O—(CO)—NH-linkage. The term "urethane acrylate polymer" is intended to mean a urethane polymer derived from polymerization of a urethane oligomer having acrylate termini —O—(CO)—CH=CH$_2$.

The term "precursor" is used herein to mean a compound which when polymerized and/or cross-linked will give rise to a desired polymer. For example, the term "perfluorinated urethane polymer precursor" denotes a compound which when treated with, for example, moisture, radiation, cross-linking agents, or combinations thereof, will give rise to the desired "perfluorinated urethane polymer" as will be described in greater detail below.

In describing chemical compounds herein, the term "lower alkyl" is used in its conventional sense to mean an alkyl group of 1 to 6 carbon atoms, e.g., methyl, ethyl, n-propyl, isopropyl, n-butyl, isobutyl, t-butyl, and the like. "Lower alkylene" refers to a difunctional saturated branched or unbranched hydrocarbon chain containing from 1 to 6 carbon atoms, and includes, for example, methylene (—CH$_2$—), ethylene (—CH$_2$CH$_2$—), propylene (—CH$_2$—CH$_2$—CH$_2$—), and the like. The term "alkylarylene" refers to a difunctional hydrocarbon moiety containing 1 or 2 monocyclic aromatic moieties, either unsubstituted phenyl rings or containing one to four substituents such as lower alkyl, halogen, nitro, or the like. "Alkylarylene" linking groups may also contain lower-alkylene spacers adjacent the aromatic rings, in which some or all of the hydrogen atoms normally present may be replaced with fluorine atoms.

The polymeric compositions which are used to formulate the gas permeable membrane of the invention are cured perfluorinated urethane polymers; the membrane itself comprises a matrix of such a polymer and, incorporated in the matrix, a gas-sensitive indicator. The cured perfluorinated urethane polymers are typically perfluorinated urethane polymer precursors cross-linked with a cross-linking agent. Generally, such precursors have the structural formula

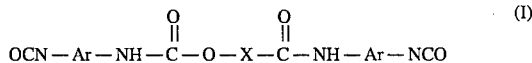

wherein Ar is a monocyclic aromatic moiety and X is a perfluorinated polyether linkage containing approximately 2 to 100, preferably 10 to 50, most preferably 15 to 25, recurring perfluorinated mer units having the structure —(CF$_2$O)—, —(CF$_2$CF$_2$O)—, or combinations thereof. Preferably, Ar is phenyl, either unsubstituted or substituted with one to four substituents which are selected so as not to interfere with polymerization or use of the cured polymer in the gas sensor; such substituents include, for example, lower alkyl (C$_1$–C$_6$), halogen, nitro, and the like.

The precursor of Formula (I) may be cross-linked using water or an organic diol HO—R—OH wherein R is a hydrocarbon substituent of about 2 to 20 carbon atoms, and in which some or all of the hydrogen atoms normally present have been replaced with fluorine atoms. Preferably, R is an alkylene linking group, i.e., an alkylene linking group containing from about 1 to 6 carbon atoms, or an alkylarylene linking group containing one or two monocyclic aromatic moieties and, depending on the number of aromatic moieties, two or three lower alkylene spacer groups, again, in which some or all of the hydrogen atoms normally present have been replaced with fluorine atoms. Exemplary organic diols include bisphenol A and hexafluorobisphenol A.

In a preferred embodiment, the precursor of Formula (I) is converted to a perfluorinated urethane acrylate precursor prior to curing, by replacing the terminal isocyanate moieties —N=C=O with acrylate termini —NH—COO—(CH$_2$)$_n$—(CO)—CH=CH$_2$ where n is typically in the range of 1 to about 6. This may be effected by reacting the diisocyanate precursor (I) with, for example, hydroxymethylmethacrylate (in which case n is 1), hydroxyethylmethacrylate (in which case n is 2), or the like. The perfluorinated urethane acrylate precursor so provided, having the structural formula

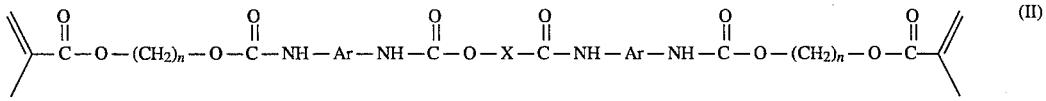

may then be cured in the presence of a suitable photoinitiator or photocatalyst using radiation. In a variation on this embodiment, the diisocyanate-terminated precursor of Formula (I) may be reacted with virtually any compound having a hydroxy terminus and a vinyl terminus, typically containing about 2 to 10 carbon atoms, to provide a vinyl-terminated precursor and to enable cross-linking.

Suitable photoinitiators for carrying out the cross-linking in the aforementioned case, i.e., to cure the perfluorinated urethane acrylate precursor of Formula (II), are radical photoinitiators that are well-known to those skilled in the art. Examples of such photoinitiators include α-alkoxy deoxybenzoins, α,α-dialkoxy deoxybenzoins, α,α-dialkoxy acetophenones, benzophenones, thioxanthones, benzils, and other compounds identified by H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53, cited supra. The disclosure of the aforementioned reference is incorporated by reference herein.

In another embodiment, the diisocyanate-terminated precursor of Formula (I) is converted to an epoxy-terminated precursor having the formula

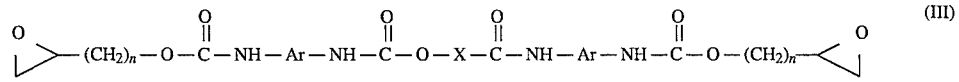

wherein Ar, X, and n are as defined above. This conversion may be readily effected by reaction of the precursor of Formula (I) with two equivalents of a compound having the structural formula

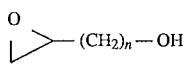

(i.e., glycidol when n is 1). This epoxy-terminated compound may then be cured with radiation in the presence of a cationic photoinitiator, e.g., a sulfonium salt, an organometallic complex such as that manufactured under the name Irgacure® by Ciba-Geigy Corporation, or the like.

One of the advantages of fabricating optical gas sensors with the aforementioned polymer compositions is that relatively low levels of cross-linking agent are required. Conventional systems typically require a very high level of cross-linking agent, on the order of 20 wt. % of the total polymeric composition. The present perfluorinated urethanes, however, typically require only about 0.5 to 5 wt. % cross-linking agent, more typically about 0.5 to 1 wt. %, to provide dimensional stability.

In formulating the gas permeable membrane, it is preferred that the above-described cross-linking reaction occur in the presence of the gas-sensitive indicator component which will then be incorporated into the polymeric matrix which serves as the membrane. the gas-sensitive indicator will generally be physically entrapped within the polymeric matrix, but it may also be covalently bound thereto. The gas-sensitive indicator is typically an inorganic complex which is a luminescent material quenchable by the oxygen, carbon dioxide, or the like, i.e., the dissolved gas which is undergoing measurement. Examples of suitable gas-sensitive indicators useful for $O_2$ determination may be found in U.K. Patent No. 2,132,348, cited supra, and include complexes of ruthenium (II), osmium (II), iridium (III), rhodium, rhenium, and chromium (III) with 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, and complexes of VO (II), Cu (II), platinum (II), and zinc (II) with porphin etioporphorin tetraphenylporphyrin, mesoporphyrin IX dimethylester, protoporphyrin IX dimethylester and octaethylporphyrin. Preferred gas-sensitive indicators for fabricating oxygen sensors are ruthenium complexes. For $CO_2$ sensors, virtually any pH-sensitive fluorescent or absorbent dye can be used, although preferred indicators include fluorescein and fluorescein derivatives such as carboxyfluorescein, seminaphthorhodafluor, seminaphthofluorescein, naphthofluorescein, hydroxypyrene trisulfonic acid, dichlorofluorescein, and the like.

The cross-linking reactions which give rise to the gas permeable membrane are preferably carried out on the fiber substrate. In a preferred embodiment, the precursor is photocurable and is cross-linked on the fiber substrate using radiation transmitted through the fiber. Alternatively, the membrane may be prepared separately and deposited on the surface of the optical fiber; in such instances, it is typically necessary to prime the fiber surface prior to deposition of the sensing membrane thereonto. An example of a suitable glass primer is γ-methacryloxypropyl trimethoxysilane. Alternatively, the distal tip of the fiber may be dipped into a solution of the precursor and the gas-sensitive indicator and taking suitable steps to cure and cross-link the solution. Once cured, the gas sensor thus formed is cleaned of residual unreacted monomer by rinsing with a solvent such as acetone. The present invention, however, minimizes the potential for unreacted monomer and rinsing may be a superfluous step.

The polymer composition—i.e., the cross-linked perfluorinated urethane polymer—will typically represent on the order of 80 to 99 wt. % of the gas permeable membrane, more typically 95 to 99 wt. % of the membrane. Any photoinitiator used will be present at customary catalytic levels, typically substantially below 1 wt. % of the membrane. Gas-sensitive indicator will generally represent on the order of 0.05 to 1.0 wt. % of the membrane.

FIG. 1 shows a typical fiber optic gas sensor arrangement. The illustrated device 11 includes a light source 12 for directing probe radiation into the device, as well as a light detector 13 for sensing and detecting radiation from the device. Device 11 includes one or more optical fibers 14 that are joined to light source 123 and to light detector 13 through a suitable junction assembly 15 at a location which is proximal of the distal end portion 16 of the optical fiber 14. As is generally known, each optical fiber 14 includes a core surrounded by a cladding or covering.

Distal end portion 16 has a distal tip 17 which is a membrane of a cross-linked perfluorinated urethane polymer matrix, and, incorporated therein, a gas-sensitive indicator as described above. The gas-sensitive indicator enables the matrix to undergo a known change in color, color intensity or other property, which change is observed by the light detector 13 in a manner generally known in the art.

Figure 3:
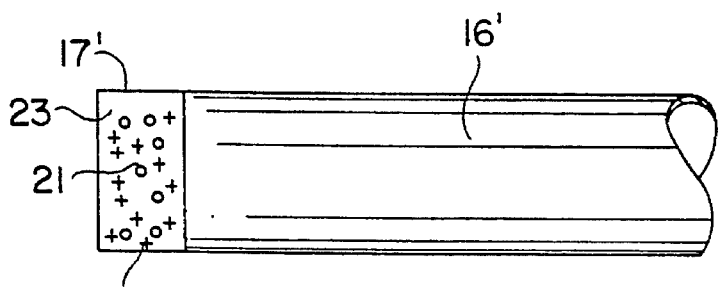
FIG. 3 is a view similar to FIG. 2 but illustrating a composite membrane arrangement.

With the embodiment illustrated in FIG. 3, a distal end portion 16' has a distal tip 17'. The tip 17' is a composite membrane suitable for multifunctional monitoring, such as for monitoring pH conditions or the like and gas concentrations. Microparticles 21 of a polymer matrix comprising a perfluorinated urethane polymer and a gas-sensitive indicator are included within the composite membrane at the distal tip 17'. Also included are other indicator components 22 such as fluorescent pH indicators. Both the gas sensor microparticles 21 and the other indicators 22 are encapsulated within a known type of gas and ion permeable hydrophilic polymer 23 which provide needed support for the microparticles therewithin.

As noted earlier, the primary utility of the present invention is in the detection and measurement of dissolved gases such as $O_2$ and $CO_2$ in the bloodstream. However, the membrane and sensor of the invention may also be used in a variety of other contexts, e.g., for on-line sensing in a flowing fluid stream.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

The objective of this example was to prepare a radiation curable fluoropolyurethane for fabricating an $H_2O$ and $H^+$ impermeable membrane with good elastomeric properties. A difunctional, isocyanate-terminated fluorinated polyether having an equivalent weight of approximately 1500 (Fluorolink™ B, obtained from Ausimont, Morristown, N.J.) was used as the polymeric precursor. The reactions which were carried out (1) replaced the diisocyanate termini of the precursor with acrylate moieties, thereby providing a photocurable compound, and (2) cured this latter acrylate-terminated compound, as follows.

Five g of Fluorolink B was weighed out and 0.43 g dry hydroxymethacrylate (HEMA) (obtained from Aldrich Chemical, Milwaukee Wis.) was added over a 4 Å molecular sieve. The reaction was permitted to proceed at room temperature uncatalyzed. After 1 hour, no apparent exotherm occurred. The reaction was incubated at approximately 20° C. for 18 hours. At that time, it was found that the preparation had not cured; accordingly, 5 μl dibutyltin laurate (obtained from Air Products and Chemicals under the name T-12) catalyst was added, and the preparation bubbled slightly.

The acrylate urethane was found to be soluble in Freon 113 trichlorotrifluoroethane; 5 μl of the cationic photoinitiator Irgacure® 500 (Ciba-Geigy) was added, and the polymer solution was thus cured under a stream of $N_2$. The structure of the polymer was verified using infrared spectroscopy.

EXAMPLE 2

The objective of this example was to prepare an $O_2$ sensor by dissolving an $O_2$-sensitive indicator in a cross-linkable, curable polymer matrix that is permeable to $O_2$. As in Example 1, Fluorolink™ B was used as the precursor to the cured perfluorinated urethane acrylate polymer which serves as the primary component of the polymer matrix. In this example, cure was effected with moisture.

1.9 mg tris(diphenyl phenanthroline) $Ru.HCl_2$ (obtained from Florida International University) was selected as the $O_2$ sensitive indicator, dissolved in 0.1 ml $CH_2Cl_2$, and miscibilized in 1.0 g of the perfluorinated prepolymer Fluorolink B. The sensor (Ensign Bickford glass-on-glass, 110μ, numerical aperture 0.39) was dipped in the polymer/gas indicator preparation and cured at 50° C. in a humidified forced air oven for 18 hours.

The following day the sensor was tested in a 39° C. tonometer using 100% He and 100% $O_2$. The signal values at 70% lamp intensity were 6000 at 100% He and 200 at 100% $O_2$. Therefore, there is greater than a 90% loss of signal at 760 mm $O_2$. Also, no substantial "burn-in" effect was observed.

EXAMPLE 3

In this example, an $O_2$ sensor was prepared using the radiation-curable perfluorinated polyurethane acrylate, as follows.

1.5 mg tris(diphenyl phenanthroline) $Ru.HCl_2$ was dissolved in 0.1 ml $CH_2Cl_2$ and miscibilized in 1.5 g of the uncured polymer prepared in Example 1. 90 mg Irgacure® 500 was added and a cleaned 110μ EB connectorized fiber was dipped in the solution to coat the distal end. The fiber was placed in a test tube under argon and exposed to an external source of ultraviolet radiation (3.4 mW) to cure for 60 seconds.

The fiber was coupled to an OSR-1 (Optical Sensors Consultants, Inc., San Carlos Calif.) and the distal end placed in a tonometer at 37° C. Under 100% Ar sparge, a 603 nm emission was observed (1500 cps); under 100% $O_2$ sparge, signal loss was greater than about 90% (with observed value at approximately 250 cps). Response time was very rapid, less than about 30 seconds. Very little signal loss was observed over the 90 minute experiment.

EXAMPLE 4

$O_2$ sensors were prepared using different polymers. In the following tables, the polyurethane/urea material was prepared as described in Example 1, and the procedure of Example 2 was used to make the sensors, except for sensor numbers 7, 8 and 9 which were prepared using the procedure of Example 3. "S.V.k" represents the Stern-Vollmer constant; as may be seen from the S.V.k data, the polyurethane/urea-based sensor displays a sensitivity approximately two-fold greater than that of the commercially available sensors.

TABLE 1

Diphenyl Phenanthrolene Ruthenium PO2 Sensor Summary

| Fiber Size | Polymer | S.V.k | Signal | % Quench | Draft Rate | Useful Life |
| --- | --- | --- | --- | --- | --- | --- |
| 240 μm | Polyurethane/urea | 0.25 | 40000 | 84% | 1.2%/hr | 5.8 hr |
| 125 μm | Polyurethane/urea | 0.018 | 15000 | 83% | 1.4%/hr | 5.0 hr |
| 240 μm | FX189 perfluoro acrylate | 0.008 | 45000 | 70% | 5.0%/hr | 1.0 hr |
| 125 μm | FX189 perfluoro acrylate | 0.007 | 2500 | 69% | 5.6%/hr | 0.75 hr |
| 240 μm | Photopolymerized polyurethane polyurea | 0.009 | 45000 | 85% | 0.8% | 6.75 hr |

EXAMPLE 5

An optical carbon dioxide sensor may be prepared using the methods and materials of the invention, as follows:

Three mg fluorescein disodium salt (Aldrich) are dissolved in 0.01M sodium bicarbonate buffer containing 0.9% NaCl. This buffered fluorescein solution (0.15 g) is then dispersed and emulsified in a solution of 1.0 g perfluorinated polyurethane dimethacrylate (80% solids, 20% ethyl acetate), and photocured on the distal end of a pretreated reactive fiber optic. The fiber optic carbon dioxide sensor so prepared has a 485 nm signal 4507, a 455 nm signal 1237 (ratio=3.64) @1% $CO_2$; the sensor has a 485 nm signal 3772, and a 455 nm signal 1111 (ratio=3.39) @10% $CO_2$. Carbon dioxide sensors may be made to have enhanced signal change by buffering in a medium closer to the pKa of the indicator, i.e., 6.8.

I claim:

1. A cross-linked gas permeable membrane useful in optical gas sensors for measuring $O_2$ or $CO_2$ in a fluid, comprising a polymeric matrix of a cured perfluorinated urethane polymer, the matrix having a gas-sensitive indicator component incorporated therein, wherein the cured perfluorinated urethane polymer comprises a perfluorinated urethane polymer precursor cross-linked with a cross-linking agent, and further wherein the precursor has the structural formula

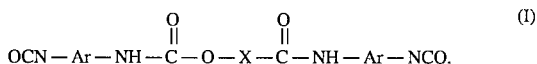

wherein Ar is a monocyclic aromatic moiety and X is a perfluorinated polyether linkage containing approximately 2 to 100 recurring perfluorinated mer units having the structure $-(CF_2O)-$, $-(CF_2CF_2O)-$, or combinations thereof.

2. The membrane of claim 1, wherein the cross-linking agent is water.

3. The membrane of claim 1, wherein the polymeric matrix comprises approximately 95 wt. % to 99.5 wt. % perfluorinated polyurethane polymer precursor and approximately 0.5 wt. % to 5 wt. % cross-linking agent.

4. The membrane of claim 1, wherein the gas-sensitive indicator is selected from the group consisting of fluorescein, carboxyfluorescein, seminaphthorhodafluor, seminaphthofluorescein, naphthofluorescein, hydroxypyrene trisulfonic acid and dichlorofluorescein.

5. The membrane of claim 1, wherein the cross-linking agent is a diol.

6. The membrane of claim 5, wherein the diol is selected from the group consisting of bisphenol A and hexafluorobisphenol A.

7. The membrane of claim 1, wherein the gas-sensitive indicator is selected from the group consisting of complexes of ruthenium (II), osmium (II), iridium (III), rhodium, rhenium, and chromium (III) with one of 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, complexes of VO (II), Cu (II), platinum (II), and zinc (II) with one of porphin etioporphorin tetraphenylporphyrin, mesoporphyrin IX dimethylester, protoporphyrin IX dimethylester and octaethylporphyrin, and combinations thereof.

8. The membrane of claim 7, wherein the gas-sensitive indicator is physically entrapped within the polymer matrix.

9. The membrane of claim 7, wherein the gas-sensitive indicator is covalently bound to the polymer matrix.

10. A cross-linked gas permeable membrane useful in optical gas sensors for measuring $O_2$ or $CO_2$ in a fluid, comprising a polymeric matrix of a cured perfluorinated urethane polymer, the matrix having a gas-sensitive indicator component incorporated therein, wherein the cured perfluorinated urethane polymer comprises a perfluorinated urethane polymer precursor having the structural formula

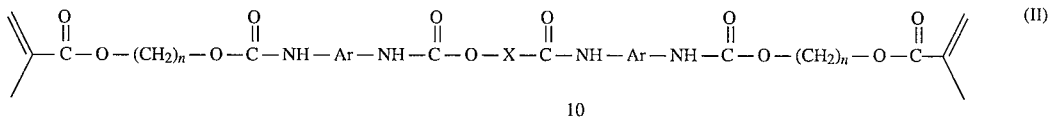

wherein Ar is a monocyclic aromatic moiety, X is a perfluorinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and further wherein the precursor is cured with a photoinitiator in the presence of radiation.

11. The membrane of claim 10, wherein the gas-sensitive indicator is selected from the group consisting of complexes of ruthenium (II), osmium (II), iridium (III), rhodium, rhenium, and chromium (III) with one of 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, complexes of VO (II), Cu (II), platinum (II), and zinc (II) with one of porphin etioporphorin tetraphenylporphyrin, mesoporphyrin IX dimethylester, protoporphyrin IX dimethylester and octaethylporphyrin, and combinations thereof.

12. The membrane of claim 11, wherein the gas-sensitive indicator is physically entrapped within the polymer matrix.

13. The membrane of claim 11, wherein the gas-sensitive indicator is covalently bound to the polymer matrix.

14. A cross-linked gas permeable membrane useful in optical gas sensors for measuring $O_2$ or $CO_2$ in a fluid, comprising a polymeric matrix of a cured perfluorinated urethane polymer, the matrix having a gas-sensitive indicator component incorporated therein, wherein the cured perfluorinated urethane polymer comprises an epoxy-terminated precursor having the structural formula

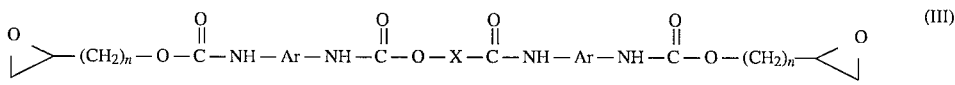

wherein Ar is a monocyclic aromatic moiety, X is a perfluorinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and further wherein the precursor is cured with a photoinitiator in the presence of radiation.

15. The membrane of claim 14, wherein the gas-sensitive indicator is selected from the group consisting of fluorescein, carboxyfluorescein, seminaphthorhodafluor, seminaphthofluorescein, naphthofluorescein, hydroxypyrene trisulfonic acid and dichlorofluorescein.

16. The membrane of claim 15, wherein the gas-sensitive indicator is physically entrapped within the polymer matrix.

17. The membrane of claim 15, wherein the gas-sensitive indicator is covalently bound to the polymer matrix.

18. An optical gas sensor for measuring $O_2$ or $CO_2$ in a fluid, comprising:

an optical waveguide having a distal end portion for monitoring a gas component within a fluid, and a proximal end portion for communication with means for receiving a signal from the distal end portion, and wherein the distal end portion has in optical communication therewith a gas sensor means comprising a cross-linked gas permeable membrane comprising a polymeric matrix of a cured perfluorinated urethane polymer, the matrix having a gas-sensitive indicator component incorporated therein, wherein the cured perfluorinated urethane polymer comprises a perfluorinated urethane polymer precursor cross-linked with a cross-linking agent, and further wherein the precursor has the structural formula

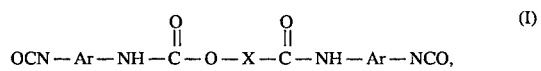

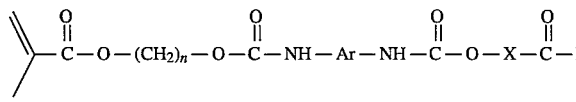 (I)

OCN—Ar—NH—C(=O)—O—X—C(=O)—NH—Ar—NCO, wherein Ar is a monocyclic aromatic moiety and X is a perfluorinated polyether linkage containing approximately 2 to 100 recurring perfluorinated mer units having the structure ‑(CF$_2$O)‑, ‑(CF$_2$CF$_2$O)‑, or combinations thereof.

19. The optical sensor of claim 18, wherein the cross-linking agent is water.

20. The optical sensor of claim 18, wherein the sensor is an O$_2$ sensor and the gas-sensitive indicator is selected from the group consisting of complexes of ruthenium (II), osmium (II), iridium (III), rhodium, rhenium, and chromium (III) with one of 2,2'-bipyridine, 1,10-phenanthroline, 4,7-diphenyl(1,10-phenanthroline), 4,7-dimethyl-1,10-phenanthroline, 4,7-disulfonated-diphenyl- 1,10-phenanthroline, 2,2'-bi-2-thiazoline, 2,2'-bithiazole, 5-bromo-1,10-phenanthroline, and 5-chloro-1,10-phenanthroline, complexes of VO (II), Cu (II), platinum (II), and zinc (II) with one of porphin etioporphorin tetraphenylporphyrin, mesoporphyrin IX dimethylester, protoporphyrin IX dimethylester and octaethylporphyrin, and combinations thereof.

21. The optical sensor of claim 14, wherein the sensor is a CO$_2$ sensor and the gas-sensitive indicator is selected from the group consisting of fluorescein, carboxyfluorescein, seminaphthorhodafluor, seminaphthofluorescein, naphthofluorescein, hydroxypyrene trisulfonic acid and dichlorofluorescein.

22. The optical sensor of claim 18, wherein the cross-linking agent is a diol.

23. The optical sensor of claim 22, wherein the diol is selected from the group consisting of bisphenol A or hexafluorobisphenol A.

24. An optical gas sensor for measuring O$_2$ or CO$_2$ in a fluid, comprising:

an optical waveguide having a distal end portion for monitoring a gas component within a fluid, and a proximal end portion for communication with means for receiving a signal from the distal end portion, and wherein the distal end portion has in optical communication therewith a gas sensor means comprising a cross-linked gas permeable membrane comprising a polymeric matrix of a cured perfluorinated urethane polymer, the matrix having a gas-sensitive indicator component incorporated therein, wherein the cured perfluorinated urethane polymer comprises a perfluorinated urethane polymer precursor having the structural formula

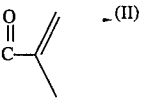 (II)

wherein Ar is a monocyclic aromatic moiety and X is a perfluorinated polyether linkage containing approximately 2 to 100 recurring perfluorinated mer units having the structure ‑(CF$_2$O)‑, ‑(CF$_2$CF$_2$O)‑, or combinations thereof, and n is an integer in the range of 0 to 6 inclusive, and further wherein the precursor is cured with a photoinitiator in the presence of radiation.

25. The optical sensor of claim 24, wherein the sensor is an O$_2$ sensor and the gas-sensitive indicator is selected from the group consisting of complexes of ruthenium (II), osmium (II), iridium (III), rhodium, rhenium, and chromium (III) with one of 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, complexes of VO (II), Cu (II), platinum (II), and zinc (II) with one of porphin etioporphorin tetraphenylporphyrin, mesoporphyrin IX dimethylester, protoporphyrin IX dimethylester and octaethylporphyrin, and combinations thereof.

26. The optical sensor of claim 24, wherein the sensor is a CO$_2$ sensor and the gas-sensitive indicator is selected from the group consisting of fluorescein, carboxyfluorescein, seminaphthorhodafluor, seminaphthofluorescein, naphthofluorescein, hydroxypyrene trisulfonic acid and dichlorofluorescein.

27. An optical gas sensor for measuring O$_2$ or CO$_2$ in a fluid, comprising:

an optical waveguide having a distal end portion for monitoring a gas component within a fluid, and a proximal end portion for communication with means for receiving a signal from the distal end portion, and wherein the distal end portion has in optical communication therewith a gas sensor means comprising a cross-linked gas permeable membrane comprising a polymeric matrix of a cured perfluorinated urethane polymer, the matrix having a gas-sensitive indicator component incorporated therein, wherein the cured perfluorinated urethane polymer comprises an epoxy-terminated precursor having the structural formula

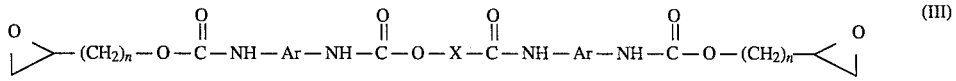 (III)

wherein Ar is a monocyclic aromatic moiety, X is a perfluorinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and further wherein the precursor is cured with photoinitiator in the presence of radiation.

28. The optical sensor of claim 27, wherein the sensor is an $O_2$ sensor and the gas-sensitive indicator is selected from the group consisting of complexes of ruthenium (II), osmium (II), iridium (III), rhodium, rhenium, and chromium (III) with one of 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, complexes of VO (II), Cu (II), platinum (II), and zinc (II) with porphin etioporphorin tetraphenylporphyrin, mesoporphyrin IX dimethylester, protoporphyrin IX dimethylester and octaethylporphyrin, and combinations thereof.

29. The optical sensor of claim 27, wherein the sensor is a $CO_2$ sensor and the gas-sensitive indicator is selected from the group consisting of fluorescein, carboxyfluorescein, seminaphthorhodafluor, seminaphthofluorescein, naphthofluorescein, hydroxypyrene trisulfonic acid and dichlorofluorescein.

30. A method for making an optical gas sensor for measuring $O_2$ or $CO_2$ in a fluid, comprising the steps of:
    (a) providing an optical waveguide having a distal end portion for monitoring a gas component within a fluid, and a proximal end portion for communication with means for receiving a signal from said distal end portion;
    (b) coating said distal end portion with a solution containing a photocurable polymeric precursor, which precursor has the structural formula taining a perfluorinated urethane polymer precursor and a gas-sensitive indicator component, to provide a precursor-coated tip; and
    (c) effecting cross-linking of said precursor, thereby providing at the distal end portion a gas sensor means comprising a cross-linked gas permeable membrane of a cured perfluorinated urethane polymer, the membrane having said gas-sensitive indicator component incorporated therein, wherein the cured perfluorinated urethane polymer comprises said perfluorinated urethane polymer precursor cross-linked with a cross-linking agent, and further wherein the precursor has the structural formula

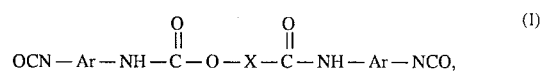

wherein Ar is a monocyclic aromatic moiety and X is a perfluorinated polyether linkage containing approximately 2 to 100 recurring perfluorinated mer units having the structure $-(CF_2O)-$, $-(CF_2CF_2O)-$, or combinations thereof.

32. The method of claim 31, wherein cross-linking is carried out by contacting the precursor-coated tip with a cross-linking agent.

33. A method for making an optical gas sensor for measuring $O_2$ or $CO_2$ in a fluid, comprising the steps of:
    (a) providing an optical waveguide having a distal end portion for monitoring a gas component within a fluid, and a proximal end portion for communication with means for receiving a signal from said distal end portion;
    (b) coating said distal end portion with a solution containing a photocurable polymeric precursor, which precursor having the structural formula

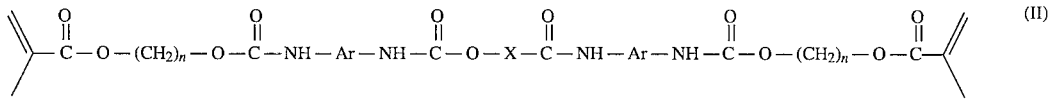

wherein Ar is a monocyclic aromatic moiety, X is a perflu-

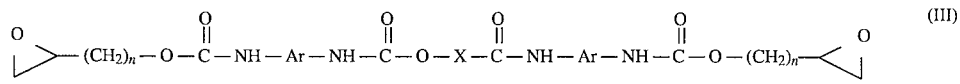

orinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and a gas-sensitive indicator component; and
    (c) effecting cross-linking of the precursor by irradiating the distal end portion through the optical waveguide using radiation of a wavelength effective to cure the precursor.

31. A method for making an optical sensor for measuring $O_2$ or $CO_2$ in a fluid, comprising the steps of:
    (a) providing an optical waveguide having a distal end portion for monitoring a gas component within a fluid, and a proximal end portion for communication with means for receiving a signal from said distal end portion;
    (b) coating said distal end portion with a solution conwherein Ar is a monocyclic aromatic moiety, X is a perfluorinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and a gas-sensitive indicator component; and
    (c) effecting cross-linking of the precursor by irradiating the distal end portion through the optical waveguide using radiation of a wavelength effective to cure the precursor.

34. A method for making an optical sensor for measuring $O_2$ or $CO_2$ in a fluid, comprising the steps of:
    (a) providing an optical waveguide having a distal end portion for monitoring a gas component within a fluid, and a proximal end portion for communication with means for receiving a signal from said distal end portion;

(b) coating said distal end portion with a solution containing a perfluorinated urethane polymer precursor and a gas-sensitive indicator component, to provide a precursor-coated tip; and (c) effecting cross-linking of said precursor, thereby providing at the distal end portion a gas sensor means comprising a cross-linked gas permeable membrane of a cured perfluorinated urethane polymer, the membrane having said gas-sensitive indicator component incorporated therein, wherein said perfluorinated urethane polymer precursor has the structural formula

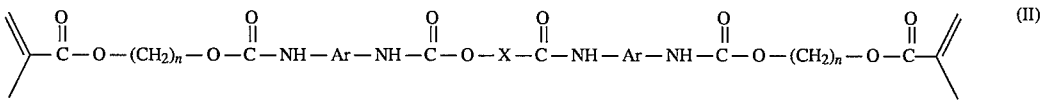

wherein Ar is a monocyclic aromatic moiety, X is a perfluorinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and further wherein the precursor is cured with a photoinitiator in the presence of radiation.

35. The method of claim 34, wherein cross-linking is carried out by irradiating the distal end portion of the optical waveguide.

36. The method of claim 34, wherein the irradiating is effected through the optical waveguide.

37. A method for making an optical sensor for measuring $O_2$ or $CO_2$ in a fluid, comprising the steps of:

(a) providing an optical waveguide having a distal end portion for monitoring a gas component within a fluid, and a proximal end portion for communication with means for receiving a signal from said distal end portion;

(b) coating said distal end portion with a solution containing a perfluorinated urethane polymer precursor and a gas-sensitive indicator component, to provide a precursor-coated tip; and (c) effecting cross-linking of said precursor, thereby providing at the distal end portion a gas sensor means comprising a cross-linked gas permeable membrane of a cured perfluorinated urethane polymer, the membrane having said gas-sensitive indicator component incorporated therein, wherein the precursor is an epoxy-terminated precursor having the structural formula

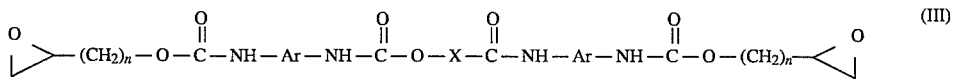

wherein Ar is a monocyclic aromatic moiety, X is a perfluorinated polyether linkage containing approximately 2 to 100 recurring perfluorinated mer units having the structure $-(CF_2O)-$, $-(CF_2CF_2O)-$, or combinations thereof, and n is an integer in the range of 0 to 6 inclusive, and further wherein the precursor is cured with a photoinitiator in the presence of radiation.

38. The method of claim 37, wherein cross-linking is carried out by irradiating the distal end portion of the optical waveguide.

39. The method of claim 37, wherein the irradiating is effected through the optical waveguide.

* * * * *